(12) United States Patent
Kim et al.

(10) Patent No.: US 9,958,603 B2
(45) Date of Patent: May 1, 2018

(54) OPTICAL FIBER FOR CHEMICAL SENSOR

(71) Applicant: GWANGJU INSTITUTE OF SCIENCE AND TECHNOLOGY, Gwangju (KR)

(72) Inventors: Bok Hyeon Kim, Gwangju (KR); Youngjoo Chung, Gwangju (KR); So Eun Kim, Gwangju (KR); Bongkyun Kim, Gwangju (KR); Tae Joong Eom, Gwangju (KR); Myoung Kyu Oh, Gwangju (KR)

(73) Assignee: Gwangju Institute of Science and Technology, Gwangju (KR)

( * ) Notice: Subject to any disclaimer, the term of this patent is extended or adjusted under 35 U.S.C. 154(b) by 0 days. days.

(21) Appl. No.: 13/949,937

(22) Filed: Jul. 24, 2013

(65) Prior Publication Data

US 2014/0037261 A1    Feb. 6, 2014

(30) Foreign Application Priority Data

Aug. 1, 2012    (KR) ........................ 10-2012-0084566

(51) Int. Cl.
| | |
|---|---|
| *G02B 6/36* | (2006.01) |
| *G02B 6/02* | (2006.01) |
| *G01N 21/3504* | (2014.01) |
| *G01N 21/552* | (2014.01) |

(52) U.S. Cl.
CPC ........... *G02B 6/02* (2013.01); *G01N 21/3504* (2013.01); *G01N 21/552* (2013.01); *G02B 6/02323* (2013.01); *G02B 6/02347* (2013.01); *G02B 6/02385* (2013.01)

(58) Field of Classification Search
CPC ........ G02B 6/02; G02B 6/32; G02B 6/02347; G02B 6/02328; G02B 6/02385; G02B 6/0229; G02B 6/032; G02B 6/1125; G02B 6/02304; G02B 6/02357; G02B 6/02366; G02B 23/2423; G02B 23/2469; G02B 2006/0325; G02B 21/0028
USPC ................................ 385/109, 129, 141–145
See application file for complete search history.

(56) References Cited

U.S. PATENT DOCUMENTS

| | | | |
|---|---|---|---|
| 6,137,928 A * | 10/2000 | Albrecht .......................... | 385/31 |
| 6,151,438 A * | 11/2000 | Espindola et al. ............. | 385/140 |
| 7,428,360 B2 * | 9/2008 | Gallagher et al. ............. | 385/125 |
| 7,567,742 B2 * | 7/2009 | Pickrell et al. ................ | 385/125 |
| 8,456,630 B2 * | 6/2013 | Bai ................................. | 356/301 |

(Continued)

FOREIGN PATENT DOCUMENTS

| | | |
|---|---|---|
| JP | 2009075065 A | 4/2009 |
| JP | 2010261958 A | 11/2010 |

(Continued)

*Primary Examiner* — Thomas A Hollweg
*Assistant Examiner* — Mary A El Shammaa
(74) *Attorney, Agent, or Firm* — Hauptman Ham, LLP

(57) ABSTRACT

An optical fiber for an optical fiber sensor and a chemical sensor using the same are disclosed. The optical fiber includes a core area, and a suspended cladding area formed around the core area and having at least one cladding hole. The core area has at least one core hole for reducing an effective refractive index of the core area. The optical fiber and the chemical sensor using the same may have improved measurement sensitivity by increasing an evanescent field fraction of existing suspended core fibers.

18 Claims, 7 Drawing Sheets

(56) References Cited

U.S. PATENT DOCUMENTS

| | | | |
|---|---|---|---|
| 2004/0071423 A1* | 4/2004 | Libori | C03B 37/0122 385/127 |
| 2004/0179796 A1* | 9/2004 | Jakobsen | C03B 37/0122 385/123 |
| 2005/0094954 A1* | 5/2005 | Pickrell | C03B 37/01297 385/123 |
| 2005/0111805 A1* | 5/2005 | Hertz | B82Y 20/00 385/125 |
| 2008/0180681 A1* | 7/2008 | Digonnet | G01C 19/722 356/477 |
| 2008/0205837 A1* | 8/2008 | Gallagher | G01N 21/3504 385/124 |

FOREIGN PATENT DOCUMENTS

| | | | | |
|---|---|---|---|---|
| KR | 20120046396 A | 5/2012 | | |
| KR | 20120057884 A | 6/2012 | | |
| WO | WO 2006068709 A1 * | 6/2006 | | C03B 37/0122 |

* cited by examiner

[Fig. 1]
--Prior Art--
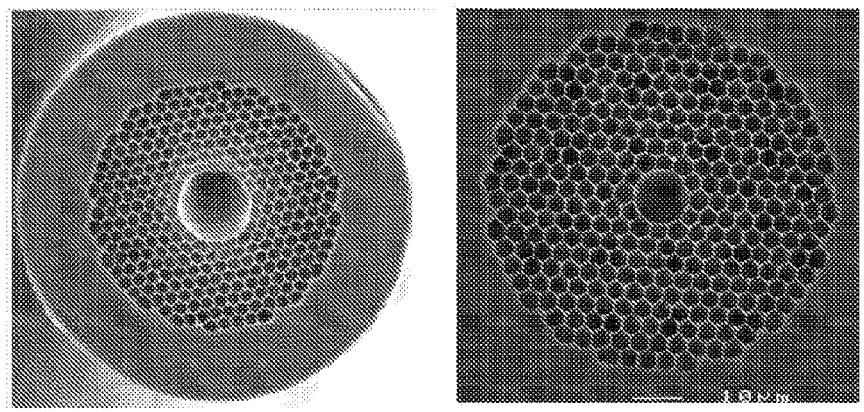
[Fig. 2]
--Prior Art--
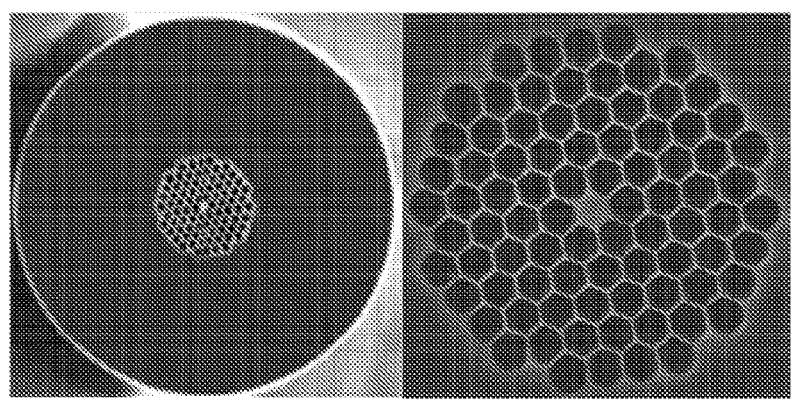

[Fig. 3]
--Prior Art--
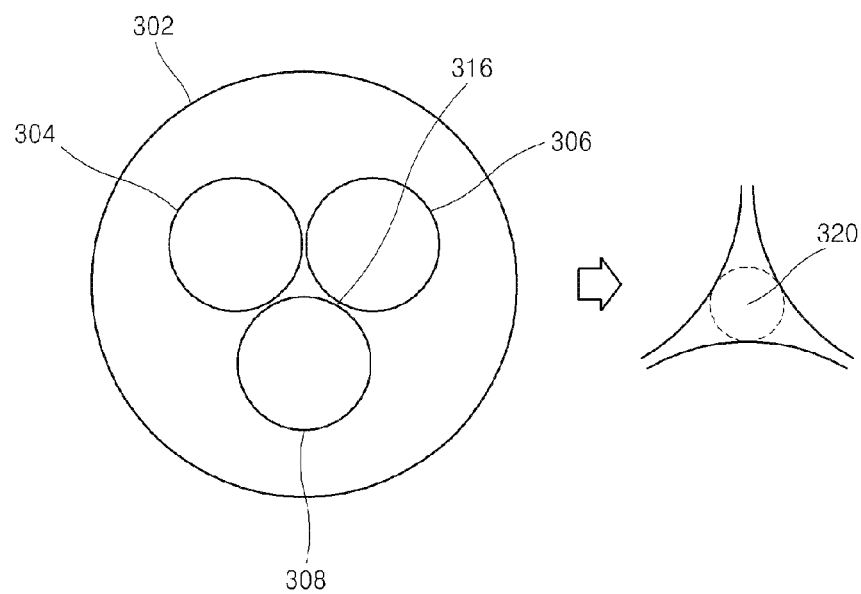
[Fig. 4]
--Prior Art--
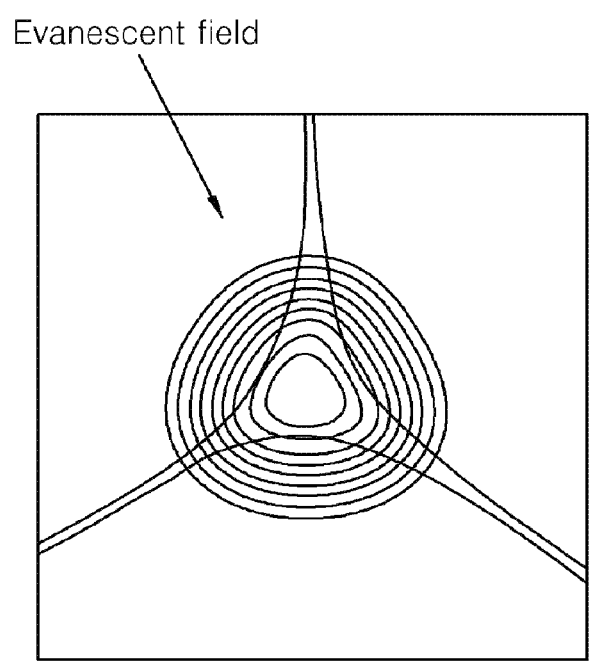

[Fig. 5]
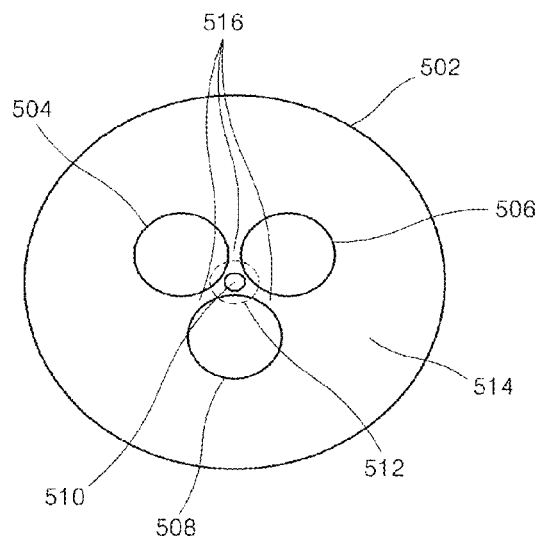
[Fig. 6]
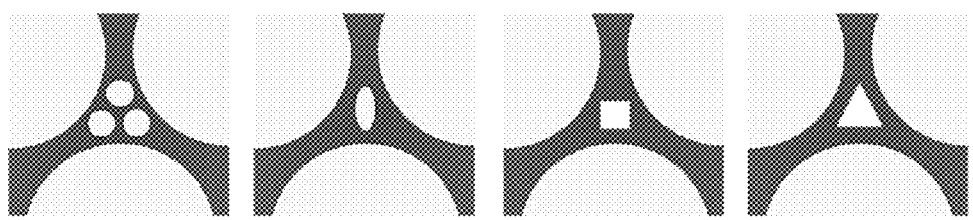
[Fig. 7]
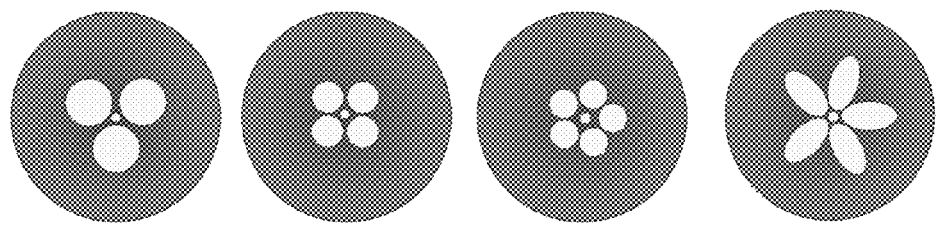

[Fig. 8]
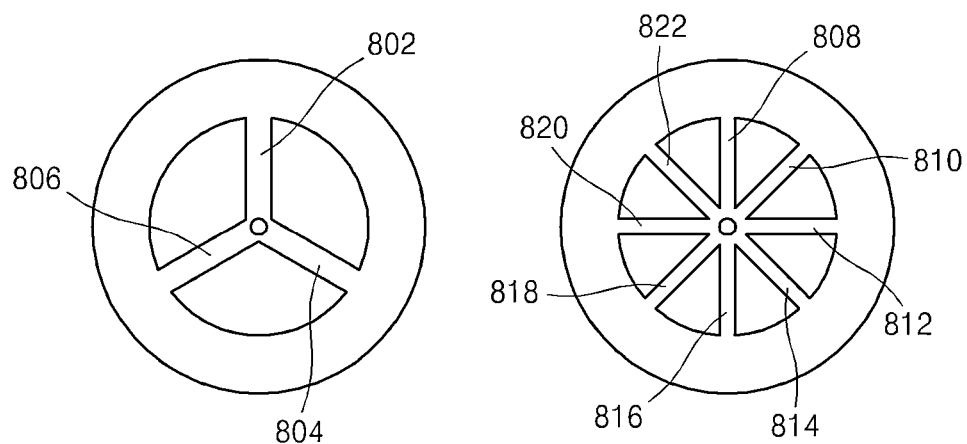
[Fig. 9]
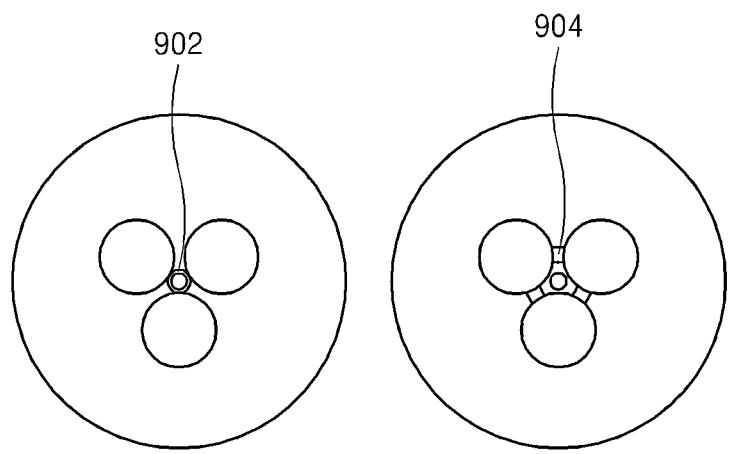

[Fig. 10]
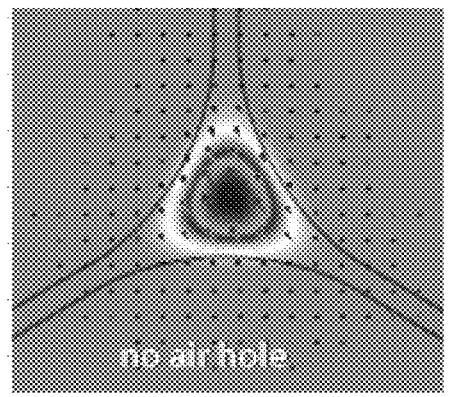
[Fig. 11]
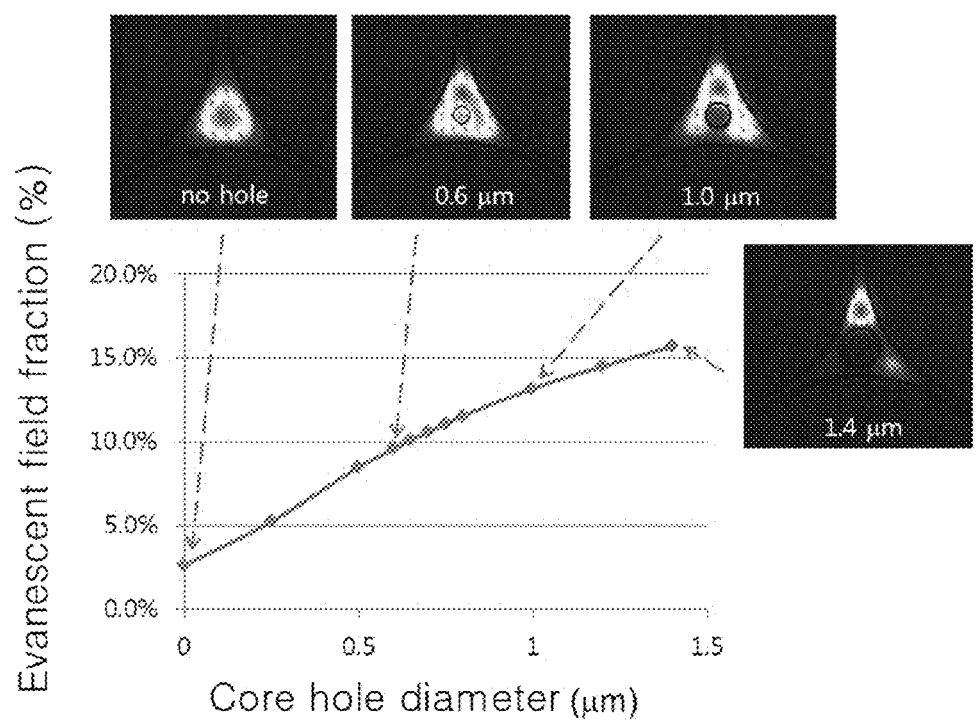

[Fig. 12]
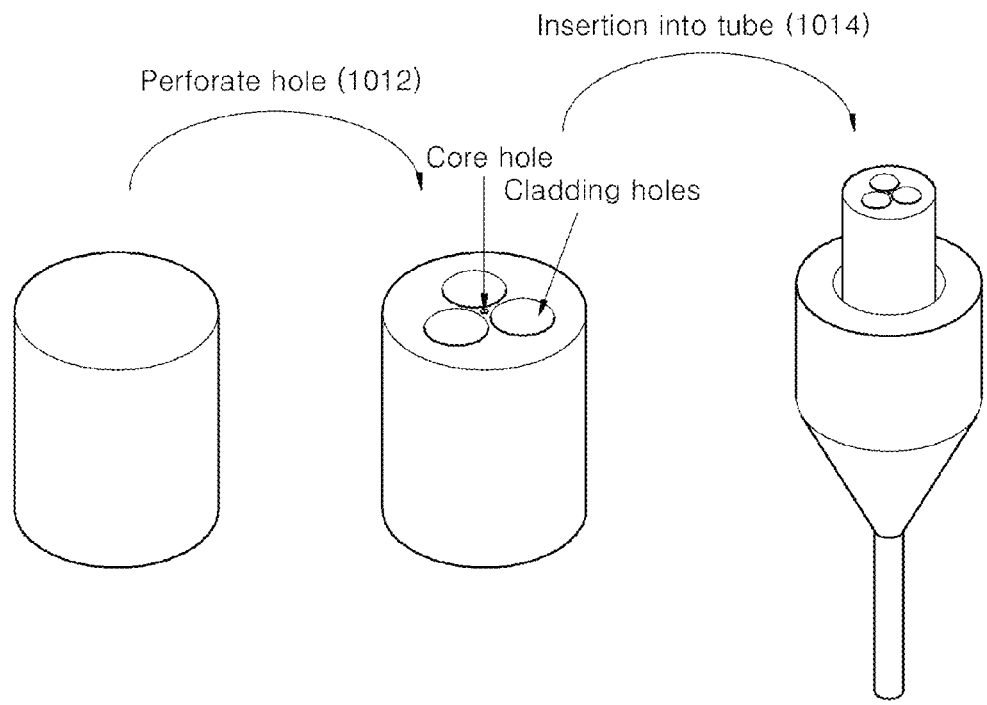
[Fig. 13]
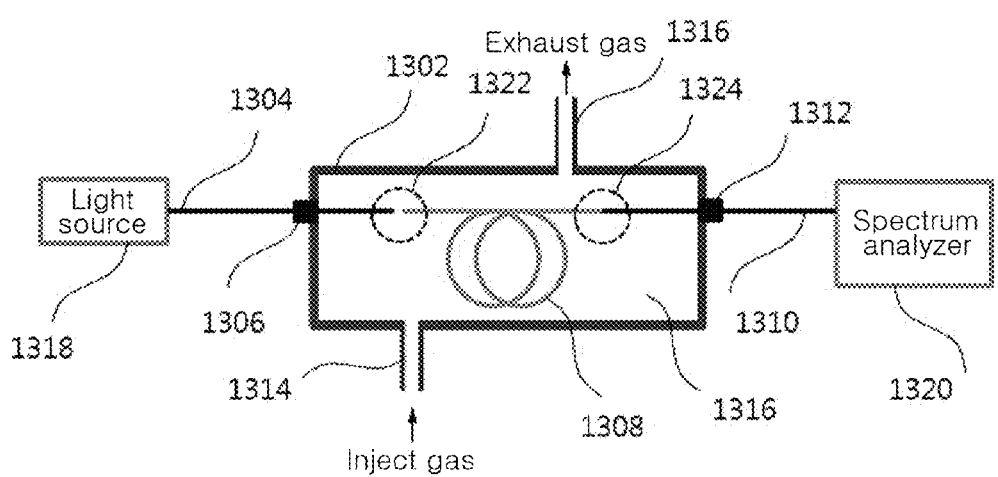

[Fig. 14]
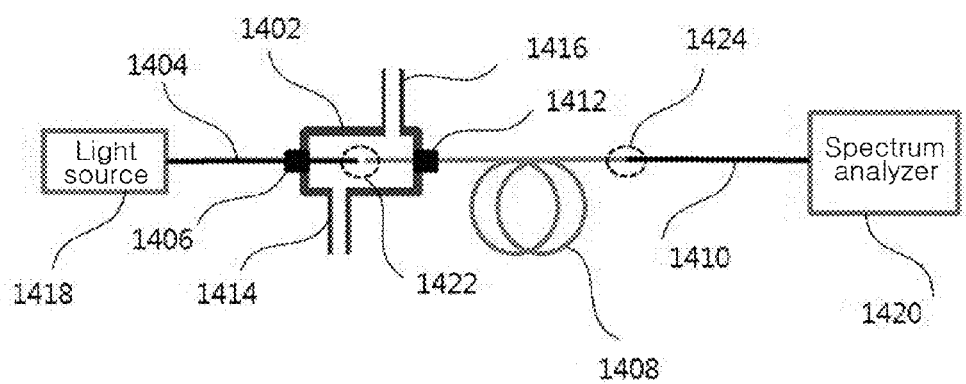
[Fig. 15]
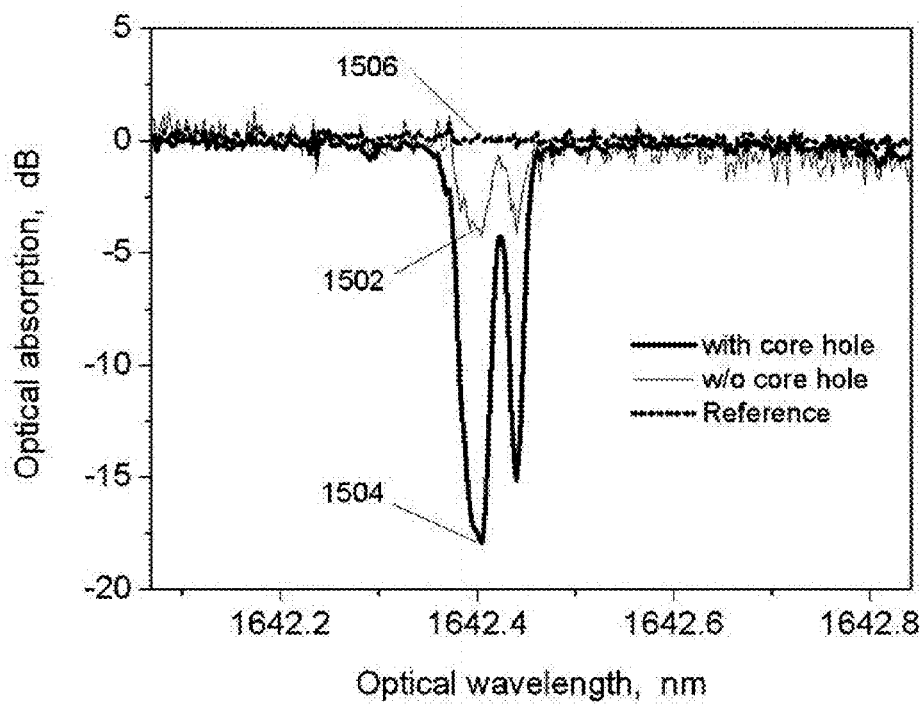

OPTICAL FIBER FOR CHEMICAL SENSOR

CROSS-REFERENCE TO RELATED APPLICATION

This application claims priority to Korean Patent Application No. 10-2012-0084566 filed on 1 Aug. 2012, and all the benefits accruing therefrom under 35 U.S.C. § 119, the contents of which is incorporated by reference in its entirety.

BACKGROUND

1. Technical Field

The present invention relates to an optical fiber for an optical fiber sensor and a chemical sensor using the same.

2. Description of the Related Art

In recent years, numerous studies into chemical sensors using optical fibers have been conducted due to driving stability, optical connectivity, convenience, and high sensitivity thereof. In particular, optical fiber-based chemical sensor technology using multiple-hole optical fibers having holes in a core area or a cladding area have recently attracted much attention. Various properties such as optical absorption, refractive index, concentration, and density of gas, liquid, or solid filled inside the hole of the optical fiber can be measured by monitoring light guided in the hole of the optical fiber in an optical fiber-based chemical sensor.

Multiple-hole optical fibers used in such a chemical sensor may be generally classified into three groups.

The first group is a photonic band gap fiber in which one hole is formed in a core area and a plurality of hole layers is formed in a cladding area, as shown in FIG. 1. The core area of the photonic band gap fiber through which light passes has a hole shape such that characteristics of gas or liquid filling the core area, such as optical absorption, refractive index, concentration, and density, can be measured with high sensitivity. However, transmission of optical fibers is sensitively influenced by the characteristics of the band gap and the geometrical structure of the hole, and it is very difficult to manufacture the optical fiber and the width of the optical transmission band is relatively very narrow.

The second group is a photonic crystal fiber in which no hole is formed in a core area and a plurality of hole layers is formed only in a cladding area, as shown in FIG. 2. Light is transmitted to a core area due to a difference between effective indexes of refraction between the core area and the cladding area in the photonic crystal fiber. Since the core of the photonic crystal optical fiber is formed of solid materials such as glass and polymer, a spectrum bandwidth of transmitted light is wider than that of the photonic band gap fiber, but the ratio of light passing through the holes of the cladding area to the entire amount of light transmitted through the optical fiber, that is, an evanescent field fraction (EFF), is so low that measurement sensitivity is very low.

The third group is a suspended core fiber 302 by which an evanescent field is increased by reducing a core area by a predetermined size or more. Large holes 304, 306, 308 having a diameter of 5 μm or more are formed as a single layer in a cladding area of the suspended core fiber 302, and a suspending wall 316 supporting the core area is formed between the cladding area and the core area. This structure is called a suspended structure. The structure of the suspended core fiber 302 is distinguished from the structure of a conventional photonic crystal fiber in which small holes approximately having a diameter of 1 μm to 4 μm are formed in a plurality of layers.

Like the photonic crystal fiber, the suspended core fiber has a wide transmission optical bandwidth and a reduced diameter of the core area, so that EFF can be increased by several dozen percent. However, the diameter of the core must be decreased below 1.5 μm in order to obtain 10% or higher EFF and, in this case, optical connectivity of the suspended core fiber to a conventional optical fiber becomes very low. Here, as shown in FIG. 3, the term "core diameter" refers to a diameter of circles adjoining core side surfaces of holes (cladding holes) 304, 306, 308 located in the cladding area.

BRIEF SUMMARY

It is an aspect of the present invention to provide an optical fiber that increases an evanescent field fraction of an existing suspended core fiber to exhibit high measurement sensitivity, and a chemical sensor using the same.

It is another aspect of the present invention to provide an optical fiber that has a wide transmission optical bandwidth and excellent optical connectivity, and can be more easily manufactured than existing optical fibers, and a chemical sensor using the same.

In accordance with one aspect of the present invention, an optical fiber for a chemical sensor is provided. The optical fiber includes: a core area; and a suspended cladding area formed around the core area and having at least one cladding hole. The core area has at least one core hole for reducing effective refractive index of the core area.

In accordance with another aspect of the present invention, a chemical sensor using an optical fiber is provided. The optical fiber includes: a core area; and a suspended cladding area formed around the core area and having at least one cladding hole. The core area has at least one core hole for reducing an effective refractive index of the core area.

The present invention is not limited to the aforementioned aspects, and other aspects and advantages of the present invention can be understood by the following description and also can be understood more clearly with reference to exemplary embodiments of the present invention. Further, it can be easily understood that the objects and advantages of the present invention can be embodied by the features set forth in the claims and combinations thereof.

BRIEF DESCRIPTION OF THE DRAWINGS

The above and other aspects, features, and advantages of the present invention will become apparent from the detailed description of the following embodiments in conjunction with the accompanying drawings, in which:

FIG. 1 is a sectional view of a photonic band gap fiber in the related art;

FIG. 2 is a sectional view of a photonic crystal fiber in the related art;

FIG. 3 is a sectional view of a suspended core fiber in the related art;

FIG. 4 is a view of an evanescent field distribution occurring in the suspended core fiber in the related art;

FIG. 5 is a sectional view of an optical fiber according to one embodiment of the present invention;

FIG. 6 is a view of examples of various core hole structures of an optical fiber according to another embodiment of the present invention;

FIG. 7 is a view of examples of various structures of cladding areas of an optical fiber according to a further embodiment of the present invention;

FIG. 8 is a view of examples of various structures of cladding areas of an optical fiber according to yet another embodiment of the present invention;

FIG. 9 is a sectional view of an optical fiber including a ring with high refractive index according to yet another embodiment of the present invention;

FIG. 10 shows a mode field distribution of a suspended core fiber having no core hole in the related art;

FIG. 11 shows a mode field distribution of an optical fiber having core holes according to the present invention and a graph depicting variation of an evanescent field fraction according to a diameter of core holes;

FIG. 12 is a view of a process of manufacturing an optical fiber and a chemical sensor according to the present invention;

FIG. 13 is a view of an optical fiber sensor for gas measurement manufactured using a suspended core fiber according to the present invention;

FIG. 14 is a view of an optical fiber sensor for gas measurement manufactured using a suspended core fiber according to the present invention; and FIG. 15 is a graph depicting light absorption characteristics of an optical fiber sensor using an optical fiber having high measurement sensitivity according to one embodiment of the present invention.

DETAILED DESCRIPTION

Exemplary embodiments of the present invention will now be described in detail with reference to the accompanying drawings. It should be understood that the present invention is not limited to the following embodiments and may be embodied in different ways, and that the embodiments are given to provide complete disclosure of the invention and to provide thorough understanding of the invention to those skilled in the art. The scope of the invention is limited only by the accompanying claims and equivalents thereof. Like components will be denoted by like reference numerals throughout the specification.

FIG. 5 is a sectional view of an optical fiber according to one embodiment of the present invention.

Referring to FIG. 5, an optical fiber 502 according to one embodiment of the invention includes a core area 512 and a cladding area. The cladding area surrounds the core area 512, and includes a monolayer with cladding holes 504, 506, 508 and an outskirt cladding region 514 surrounding the cladding holes. The optical fiber 502 further includes support walls 516 that connects the core area 512 to the outskirt cladding region. For reference, the structure of the cladding area including the monolayered cladding holes and the support walls is defined as a suspended structure in the present invention. The cladding holes may have a diameter of 5 μm or more. A larger diameter of the cladding holes allows easier introduction of gas, liquid, or solid material into the cladding holes for measurement. Preferably, the cladding holes have a diameter of 10 μm or more. More preferably, the cladding holes have a diameter of 20 μm or more. In addition, it should be noted that the cladding holes have a smaller diameter than a radius of the suspended core fiber.

The core area 512 serves to condense input light like a core of a conventional optical fiber. However, the optical fiber used in a chemical sensor can achieve higher measurement sensitivity only when light passing through the core area 512 is dispersed to the cladding holes of the cladding area.

In the related art, a method of reducing a size of a core area has been attempted to obtain high measurement sensitivity. That is, the diameter of the core is reduced by narrowing an interval between cladding holes 304, 306, 308 in FIG. 3. When the diameter of the core is reduced to 2 μm or less, light can be considerably dispersed from the core area to the cladding area. In this method, however, since the diameter of the core becomes excessively small, optical connectivity to a conventional optical fiber having a diameter of 8 μm to 10 μm is significantly lowered. Further, in order to form a very small core in the optical fiber, a jacketing process and/or a rod-in-tube optical fiber drawing process must be performed several times. Further, upon drawing of the optical fiber, substantial time is consumed to expand the cladding holes and the process becomes complex.

Thus, in the present invention, a core hole 510 is formed in the core area 512 to obtain high measurement sensitivity through a more convenient method without suffering such problems. Further, the core hole 510 is filled with a low refractive index material, such as air, capable of lowering an effective refractive index of the core area. The core hole 510 is formed in the core area 512 to lower the effective refractive index of the core area 512 such that light distributed in the core area 512 can be dispersed to the cladding holes 504, 506, 508 located in the cladding area.

Next, a principle of enhancing measurement sensitivity of an optical fiber according to the present invention and improving optical connectivity of the optical fiber to a conventional optical fiber will be described in detail.

For example, if the cladding holes 504, 506, 508 have a refractive index of 1 and the core area 512 free from a core hole 510 has a refractive index of 1.4, a difference in refractive index between the core area 512 and the cladding holes is 0.4. However, if the core hole 510 filled with a low refractive index material is formed in the core area 512 as in the present invention, an overall effective refractive index of the core area 512 is lower than 1.4. Accordingly, an effective refractive index difference between the core area 512 and the cladding holes becomes lower than 0.4, and an evanescent field fraction, that is, an amount of light dispersed from the core area to the cladding holes, increases.

As a result, according to the present invention, as the ratio of a sectional area of the core area 512 to a sectional area of the core hole 510 increases, a higher evanescent field fraction (EFF) can be obtained. Thus, in order to obtain a high evanescent ratio, the number or cross-section of the core hole 510 may be increased.

By the aforementioned principle, the sensitivity of the chemical sensor using the optical fiber according to the present invention becomes higher than a typical fiber optic chemical sensor in the art. Due to the formation of the core hole 510, a mode field diameter (MFD) increases, thereby improving optical connectivity of the optical fiber according to the present invention to a conventional optical fiber. Here, the term "mode field diameter" refers to a diameter at which the intensity of light decreases to $1/e^2$ of a maximum value. Further, the optical fiber according to the present invention has an optical transmission bandwidth wider than that of an optical fiber for a chemical sensor in the art. In addition, characteristics of a target material can be more accurately and rapidly measured using the optical fiber according to the present invention.

Further, the core hole 510 may be filled with a low refractive index material, such as air, capable of lowering the effective refractive index of a core area. The material may be a liquid or solid material, the refractive index of which is lower than that of a material constituting a core or a cladding.

For example, when an optical fiber is formed of silica glass ($SiO_2$), the effective refractive index of the core area 512 may be lowered by filling the core hole 510 with a silica glass incorporated with dopants, such as fluorine (F) or boron (B), the refractive index of which is lower than that of the silica glass.

FIG. 6 is a view of examples of various core holes of an optical fiber according to another embodiment of the present invention.

Referring to FIG. 6, at least one core hole 510 may be formed in the core area 512. Further, as shown in FIG. 6, the core hole 510 may have various shapes such as a circle, an ellipse, or a polygon.

FIGS. 7 and 8 are a view of examples of various cladding areas of an optical fiber according to a further embodiment of the present invention.

Referring to FIG. 7, cladding holes formed in the cladding area of the optical fiber according to the present invention may have various shapes. Further, as shown in FIG. 7, the cladding area of the optical fiber according to the invention may have various shapes and numbers of cladding holes. When the cladding holes are not circular, the diameter of the cladding holes refers to a diameter of a virtual circle having the same cross-sectional area as the cladding hole. In FIG. 8, the cladding area may include one or more fan-shaped cladding holes. The thickness or length of support walls 802, 804, 806, 808, 810, 812, 814, 816, 818, 820 and 822 may differ according to the number of or interval between the cladding holes.

FIG. 9 is a sectional view of an optical fiber including a high refractive index ring according to yet another embodiment of the present invention.

As described above, an important factor in the suspended core fiber together with the evanescent field fraction according to the effective refractive index of the core area is optical connectivity to a conventional optical fiber. Accordingly, a core area of an optical fiber according to this embodiment may include high refractive index rings 902, 904 to enhance optical connectivity, as shown in FIG. 9. For example, if the core area and the cladding area are formed of the same material, the core or cladding holes can be deformed when the optical fiber is fused by the conventional fusion splicing process, resulting severe connection loss during the optical connection. In this case, a high refractive index ring may be formed to restrain connection loss, thereby facilitating optical connection. As shown in FIG. 9, the high refractive index ring 902 may be formed on an inner surface of the core hole, or the high refractive index ring 904 may be circularly formed on support walls outside the core hole, or between the core hole and the cladding area. In the case of an optical fiber made by silica glass, the high refractive index ring can be formed of silica incorporated with high refractive index materials, such as germanium (Ge), titanium (Ti), aluminum (Al), phosphorus (P), lead (Pb), or bismuth (Bi).

FIG. 10 shows a mode field distribution of a suspended core fiber having no core hole and having a core diameter of about 2 μm in the related art, FIG. 11 shows mode field distributions of optical fibers having core holes according to the present invention and having a core diameter of about 2 μm and a graph of depicting variation of an evanescent field fraction (EFFs) according to the diameter of the core holes.

Referring to FIG. 10, since light is strongly confined at a core area in the suspended core fiber having no core hole in the art, MFD is as low as about 2 μm and an evanescent field fraction is as low as about 2.6%. Accordingly, measurement sensitivity is very low in the sensor made by the suspended core fiber. Further, when the optical fiber in the art is connected to a conventional optical fiber (MFD: 8 to 10 μm) which has a relatively larger MFD than that of the suspended core fiber in the art, optical connection loss is very large due to an MFD mismatch between the two optical fibers.

On the other hand, referring to FIG. 11, according to the present invention, as the diameter of the core hole formed in the core area increases, the evanescent field fraction also increases. Referring to FIG. 11, when the core holes have diameters of 0.6 μm, 1.0 μm, and 1.4 μm, respectively, evanescent field fractions increase to 9.6%, 13.2%, and 15.7%, respectively. In addition, the connection loss in the sensor made by the fiber according to the present invention is smaller than that of the sensor made by the fiber in the art, thus noise figure of the sensor according to the present invention is improved. Thus, the optical fibers according to the present invention and the chemical sensor using the same have higher measurement sensitivity and higher measurement speed than optical fibers in the related art.

In the graph of FIG. 11, it can be seen that distribution of light is expanded from the core toward the cladding holes and the support wall as the diameter of the core hole increases and thus MFD also increases. Thus, the optical fiber according to the invention has a larger MFD than that of a typical optical fiber in the art having no core hole, and thus, provides high optical connectivity when the optical fiber according to the invention is connected to a conventional optical fiber.

FIG. 12 is a view of a process of manufacturing an optical fiber for a chemical sensor according to the present invention.

Drilling or extrusion process is used to manufacture an optical fiber having a suspended structure. In the drilling process, a plurality of circular holes is perforated around a core of a rod-shaped optical fiber preform, which in turn is drawn into an optical fiber by fiber drawing process. During the drawing process, the size and the shape of the cladding holes, core holes, and support walls can be changed by controlling air pressures inside the core and cladding holes. When positive air pressure is applied to the cladding holes upon drawing of the optical fiber, the cladding holes are expanded and the support wall becomes sufficiently thin, so that light can be transmitted to the core area in the resulted fiber.

In the extrusion process, an optical fiber preform having a desired core size and shape can be made using extrusion dies appropriately designed. Various sizes and shapes of core holes, cladding holes, and support walls such as a circle, ellipse, fan shape, and polygon may be formed by extrusion, and the support wall can be made sufficiently thin.

Referring to FIG. 12, first, core and cladding holes are perforated in a rod shaped optical fiber preform (1012). Through this process, a core area including the core hole and a cladding area including the cladding hole are introduced in the optical fiber.

The core hole can be more conveniently formed using a tube collapsing technique instead of the drilling process. An tube material having a proper tube inner diameter (concerning to a core hole diameter) can be formed first by applying heat to the tube material having a certain inner and outer diameter and applying pressure from the exterior to the interior of the tube, and finally a cladding hole can be drilled around the core hole to prepare an optical fiber preform.

The primary fiber preform for an optical fiber made in this way is inserted into a secondary tube (1014) to prepare an optical fiber preform. Finally, an optical fiber for a chemical sensor according to the invention is fabricated by fiber drawing process. As mentioned before, the size and the shape of the cladding holes, core holes, and support walls can be changed to have a predetermined size and shapes by controlling air pressures inside the core and cladding holes during the fiber drawing process.

An optical fiber for a chemical sensor having a core hole and cladding holes may be prepared by the extrusion process in addition to the drilling process. First, an extrusion die having a properly designed structure for a cross-sectional shape of an optical fiber is used in an extrusion machine, and an optical fiber preform is fabricated by heating, pressurizing, and extruding an optical fiber preform forming material. Next, an optical fiber for a chemical sensor according to the invention is obtained by performing the aforementioned optical fiber drawing process. Extrusion may provide a wider variety of structures to the optical fibers, as compared with drilling.

FIG. 13 is a view of an optical fiber sensor for gas measurement consisted of a suspended core fiber, sensor housing, and other components according to the present invention.

A suspended core fiber 1308 is placed in an optical fiber sensor housing 1302. An input optical fiber 1304 connected to a light source 1318 is connected to an interior of the housing by a gasket 1306 mounted on the housing, and the input optical fiber 1304 and the suspended core fiber 1308 are optically connected to each other in an optical input connection part 1322. The suspended core fiber 1308 and an output optical fiber 1310 are optically connected to each other in an optical output connection part 1324. The output optical fiber is connected to the exterior of the housing through the gasket 1312, and then is connected to a spectrum analyzer 1320. A gas inlet 1314 and a gas outlet 1316 mounted on the housing 1302 may be provided, and a measurement target gas 1316 is introduced and exhausted therethrough. For convenience, a gas valve, a gas supply pump, and a gas evacuation pump can be connected to the gas inlet 1314 and the gas outlet 1316. The gaskets 1306, 1312 prevent the gas from leaking between the inside and outside of the housing when the input optical fiber and the output optical fiber pass through the housing to be mounted.

Light output from the light source 1318 passes through the input optical fiber 1304, enters the suspended core fiber 1308, passes through the output optical fiber 1310, and finally put into the spectrum analyzer or light detection unit 1302. The kind, concentration, and other characteristics of a gas can be determined by analyzing the optical absorption spectrum or the transmitted light intensity at a specific wavelength influenced by gas using the sensor system.

In at least one of an optical input connection 1322 and an optical output connection 1324, a butt coupling method is used for optically connecting the optical fibers to be separated at specific intervals from each other, whereby the measurement target gas filled inside the housing can flow into the holes of the suspended core fiber through a gap between the two optical fibers. A fiber collimator or a collimating lens can be used to increase optical connectivity during the butt coupling. In FIG. 13, the optical input connection 1322 is optically connected by the butt coupling, and the optical output connection 1324 is conducted by a fusion slicing method.

Since the cladding holes inside the suspended core fiber is blocked from the exterior of the optical fiber when the suspended core fiber is optically connected by the fusion splicing method, a volume of the housing is reduced to contribute to weight reduction of the sensor by adjusting a location of the gasket 1412 and moving the optical output connection part 1424 to the outside of the housing 1402.

FIG. 15 is a graph depicting optical absorption characteristics of an optical fiber sensor using an optical fiber having high measurement sensitivity according to one embodiment of the present invention. An experiment was conducted using a suspended core fiber having three cladding holes in a cladding area and one core hole at the center of a core area, as shown in FIG. 5. The optical fiber diameter, cladding hole diameter, core diameter, and core hole diameter were 125 μm, 31 μm, 3 μm, and 0.7 μm, respectively. In this experiment, the optical fiber had a length of 5 m. In a comparative example, a conventional suspended core fiber having the same structure but no holes in the core was used to evaluate optical absorption characteristics under the same conditions.

FIG. 15 shows optical absorption spectra when optical fibers were exposed to methane (CH4) gas at a same gas pressure. It can be observed that optical absorption occurred by methane gas at 1642.4 nm. It can be seen that, in an optical fiber sensor using a conventional suspended core fiber having no core hole, the intensity of optical absorption 1502 was as small as 4.1 dB, whereas in an optical fiber sensor using a suspended core fiber having a core hole according to the present invention, the intensity of optical absorption 1504 significantly increased to 17.9 dB. For reference, optical absorption 1506 of the optical fiber sensor using the suspended core fiber when methane gas was not injected is also shown. Thus, it can be seen that when the core hole is formed in the suspended core fiber according to the present invention, measurement sensitivity of the sensor can be increased by 4.3 times or more.

A concentration of a specific material can be calculated from the measured intensity of optical absorption using the following Lambert-Beer equation. The optical absorption coefficient, α, is proportional to the concentration C of a material causing the optical absorption. Thus, the concentration of the specific gas can be calculated using the extinction coefficient, ε, and the absorption intensity, dB, at the optical absorption wavelength of the material.

$$dB = 10 log_{10}\left(\frac{I_0}{I}\right) = 4.343 \cdot \alpha \cdot f \cdot t \quad \langle \text{Equation 1} \rangle$$

$$\alpha = C \cdot \varepsilon$$

$$C = dB / (4.343 \cdot \varepsilon \cdot f \cdot t)$$

In Equation 1, $I_0$, I, t, and f denote an intensity of input light, an intensity of output light, a length of an optical fiber, and an evanescent field fraction (EFF), respectively. Thus, when an optical absorption limit value dB capable of being measured according to a performance limit of a spectrum analyzer or light detection unit is given, the concentration (C) of a material can be measured more accurately as the evanescent field fraction (EFF) f increases, thereby improving measurement sensitivity.

The present invention provides an optical fiber and a chemical sensor using the same, which have improved measurement sensitivity by increasing an evanescent field fraction of existing suspended core fibers.

Further, the present invention provides an optical fiber, which has a wide transmission optical band width, has excellent optical connectivity, and can be more easily manufactured than existing optical fibers, and a chemical sensor using the same.

Although some exemplary embodiments have been described herein, it should be understood by those skilled in the art that these embodiments are given by way of illustration only, and that various modifications, variations and alterations can be made without departing from the spirit and scope of the invention. The scope of the present invention should be defined by the appended claims and equivalents thereof.

What is claimed is:

1. An optical fiber for measuring characteristics of gas or liquid, comprising:
    a core area, wherein the core area has a core hole for reducing an effective refractive index of the core area and for increasing evanescent field fraction, and wherein the core hole extends an entirety of a length of the optical fiber; and
    a suspended cladding area formed around the core area and having monolayered cladding holes,
    wherein the gas or liquid is directly introduced into the suspended cladding area,
    wherein light passing through the core area is dispersed to the suspended cladding area,
    wherein the cladding holes are formed continuously along with the longitudinal direction of the optical fiber, and
    wherein the core hole has a smaller diameter than the cladding holes.

2. The optical fiber according to claim 1, wherein the core area comprises a high refractive index ring having a higher refractive index than a periphery of the core hole.

3. The optical fiber according to claim 2, wherein the high refractive index ring is disposed on an inner surface of the core hole.

4. The optical fiber according to claim 2, wherein the high refractive index ring is disposed between the monolayered cladding holes.

5. The optical fiber according to claim 2, wherein the high refractive index ring extends around the core hole of the core area.

6. The optical fiber according to claim 1, wherein the core hole is filled with a material having a lower refractive index than a material around the core hole.

7. The optical fiber according to claim 1, the core hole has a shape of a circle, an ellipse, or a polygon.

8. The optical fiber according to claim 1, the cladding holes have a shapes of a circle, an ellipse, a polygon, or a fan.

9. The optical fiber according to claim 1, wherein diameters of the monolayered cladding holes are equal to or larger than 10 µm.

10. A chemical sensor using an optical fiber and used for measuring characteristics of gas or liquid, the optical fiber comprising:
    a core area, wherein the core area has a core hole for reducing an effective refractive index of the core area and for increasing evanescent field fraction, and wherein the core hole extends an entirety of a length of the optical fiber; and
    a suspended cladding area formed around the core area and having monolayered cladding holes,
    wherein the gas or liquid is directly introduced into the suspended cladding area,
    wherein light passing through the core area is dispersed to the suspended cladding area,
    wherein the cladding holes are formed continuously along with the longitudinal direction of the optical fiber, and
    wherein the core hole has a smaller diameter than the cladding holes.

11. The chemical sensor according to claim 10, wherein the core area comprises a high refractive index ring having a higher refractive index than a periphery of the core hole.

12. The chemical sensor according to claim 11, wherein the high refractive index ring is disposed on an inner surface of the core hole.

13. The chemical sensor according to claim 11, wherein the high refractive index ring is disposed between the monolayered cladding holes.

14. The chemical sensor according to claim 11, wherein the high refractive index ring extends around the core hole of the core area.

15. The chemical sensor according to claim 10, wherein the core hole is filled with a material having a lower refractive index than a material around the core hole.

16. The chemical sensor according to claim 10, the core hole has a shape of a circle, an ellipse, or a polygon.

17. The chemical sensor according to claim 10, the cladding holes have a shapes of a circle, an ellipse, a polygon, or a fan.

18. The chemical sensor according to claim 11, wherein diameters of the monolayered cladding holes are equal to or larger than 10 µm.

* * * * *